(12) United States Patent
Thompson

(10) Patent No.: US 6,878,283 B2
(45) Date of Patent: Apr. 12, 2005

(54) FILTER CARTRIDGE ASSEMBLIES AND METHODS FOR FILTERING FLUIDS

(75) Inventor: Ralph P. Thompson, Oklahoma City, OK (US)

(73) Assignee: Renal Solutions, Inc., West Lafayette, IN (US)

( * ) Notice: Subject to any disclaimer, the term of this patent is extended or adjusted under 35 U.S.C. 154(b) by 369 days.

(21) Appl. No.: 09/995,888

(22) Filed: Nov. 28, 2001

(65) Prior Publication Data

US 2003/0098270 A1 May 29, 2003

(51) Int. Cl.[7] ............................................. B01D 24/12
(52) U.S. Cl. ................... 210/650; 210/232; 210/257.1; 210/322; 210/323.1; 210/323.2; 422/261; 422/255; 604/221; 604/416
(58) Field of Search ............................... 210/650, 232, 210/257.1, 322, 323.1, 323.2; 422/261, 255; 604/221, 416

(56) References Cited

U.S. PATENT DOCUMENTS

| | | |
|---|---|---|
| 2,328,381 A | 8/1943 | Jaffe |
| 3,357,563 A | 12/1967 | Sicard |
| 3,520,298 A | 7/1970 | Lange |
| 3,545,438 A | 12/1970 | De Vries |
| 3,669,878 A | 6/1972 | Marantz et al. |
| 3,669,880 A | 6/1972 | Marantz et al. |
| 3,685,680 A | 8/1972 | Tenckhoff et al. |
| 3,697,410 A | 10/1972 | Johnson et al. |
| 3,697,418 A | 10/1972 | Johnson |
| 3,703,959 A | 11/1972 | Raymond |
| 3,850,835 A | 11/1974 | Marantz et al. |
| 3,888,250 A | 6/1975 | Hill |
| 3,939,069 A | 2/1976 | Granger et al. |
| 3,989,622 A | 11/1976 | Marantz et al. |
| 3,989,625 A | 11/1976 | Mason |
| 4,025,608 A | 5/1977 | Tawil et al. |
| 4,042,672 A | 8/1977 | Brugger et al. |
| 4,088,456 A | 5/1978 | Giorgi et al. |
| 4,190,047 A | 2/1980 | Jacobsen et al. |

(Continued)

FOREIGN PATENT DOCUMENTS

| | | |
|---|---|---|
| EP | 000152717 A1 | 8/1985 |
| FR | 2 585 251 A1 | 5/1985 |
| FR | 2585251 | 1/1987 |
| GB | 1 467 880 | 3/1977 |
| GB | 1 470 206 | 4/1977 |
| JP | 59 046964 | 3/1984 |
| JP | 3-242206 | 10/1991 |
| JP | 08187284 | 7/1996 |
| SU | 1770285 A1 | 10/1992 |

OTHER PUBLICATIONS

"Augmentation of Efficiency by Continuous Flow Sorbent Regeneration Peritoneal Dialysis", A. Gorden et al., vol. XXII Trans. Amer. Soc. Artif. Int. Organs, 1976, pp. 599–604.

(Continued)

*Primary Examiner*—Minh-Chau T. Pham
(74) *Attorney, Agent, or Firm*—Kilyk & Bowersox, P.L.L.C.

(57) ABSTRACT

Filter cartridge assemblies and housings are provided and include a tubular housing having an inner wall, an outer wall, a first end, and a second end. The housings include inner walls with shoulders or other radially-inwardly extending flow directors at the intersections of adjacent sections of the tubular body. The assemblies include a plurality of filter media sections within the housing, and each of the plurality of filter media sections preferably has a different filter media composition. One or more of the filter media sections traverses one or more of the shoulders or other radially-inwardly extending flow directors such that the flow directors evenly direct the flow of fluid through the assembly. The assemblies find particular applicability in dialysis systems.

45 Claims, 6 Drawing Sheets

U.S. PATENT DOCUMENTS

| | | | |
|---|---|---|---|
| 4,192,748 A | 3/1980 | Hyden | |
| 4,213,859 A | 7/1980 | Smakman et al. | |
| 4,256,718 A | 3/1981 | McArthur et al. | |
| 4,360,507 A | 11/1982 | McArthur et al. | |
| 4,412,917 A | 11/1983 | Ahjopalo | |
| 4,460,555 A | 7/1984 | Thompson | |
| 4,473,449 A | 9/1984 | Michaels et al. | |
| 4,474,853 A | 10/1984 | Watanabe | |
| 4,484,599 A | 11/1984 | Hanover et al. | |
| 4,495,129 A | 1/1985 | Newberry et al. | |
| 4,521,528 A | 6/1985 | Kovach | |
| 4,558,996 A | 12/1985 | Becker | |
| 4,560,472 A | 12/1985 | Granzow et al. | |
| D282,578 S | 2/1986 | Humphreys et al. | |
| 4,650,587 A | 3/1987 | Polak et al. | |
| 4,680,122 A | 7/1987 | Barone | |
| 4,738,668 A | 4/1988 | Bellotti et al. | |
| 4,765,907 A | 8/1988 | Scott | |
| 5,004,459 A | 4/1991 | Peabody et al. | |
| 5,032,261 A | 7/1991 | Pyper | |
| 5,034,124 A | 7/1991 | Kopf | |
| 5,035,805 A | 7/1991 | Freeman et al. | |
| 5,151,082 A | 9/1992 | Gorsuch et al. | |
| 5,173,125 A | 12/1992 | Felding | |
| 5,350,505 A | 9/1994 | Tang | |
| 5,427,683 A | 6/1995 | Gershon et al. | |
| 5,489,385 A * | 2/1996 | Raabe et al. ................. | 210/448 |
| 5,498,338 A | 3/1996 | Kruger et al. | |
| 5,520,632 A | 5/1996 | Leveen et al. | |
| 5,549,674 A | 8/1996 | Humes et al. | |
| 5,595,909 A | 1/1997 | Hu et al. | |
| 5,597,805 A | 1/1997 | Breborowicz et al. | |
| 5,631,025 A | 5/1997 | Shockley et al. | |
| 5,641,405 A | 6/1997 | Keshaviah et al. | |
| 5,679,231 A | 10/1997 | Alexander et al. | |
| 5,704,915 A | 1/1998 | Melsky et al. | |
| 5,712,154 A | 1/1998 | Mullon et al. | |
| 5,782,796 A | 7/1998 | Din et al. | |
| 5,824,213 A | 10/1998 | Utterberg | |
| 5,938,634 A | 8/1999 | Packard | |
| 5,944,684 A | 8/1999 | Roberts et al. | |
| 5,955,450 A | 9/1999 | Breborowicz et al. | |
| 5,968,966 A | 10/1999 | Bergström | |
| 5,980,481 A | 11/1999 | Gorsuch | |
| 5,984,891 A | 11/1999 | Keilman et al. | |
| 6,017,942 A | 1/2000 | Bergström | |
| 6,074,359 A | 6/2000 | Keshaviah et al. | |
| 6,117,122 A | 9/2000 | Din et al. | |
| 6,146,536 A | 11/2000 | Twardowski | |
| 6,196,992 B1 | 3/2001 | Keilman et al. | |
| 6,217,540 B1 * | 4/2001 | Yazawa et al. ............ | 604/4.01 |
| 6,274,103 B1 * | 8/2001 | Taylor ........................ | 422/261 |
| 6,284,131 B1 | 9/2001 | Hogard et al. | |
| 6,284,139 B1 | 9/2001 | Piccirillo | |
| 6,293,921 B1 | 9/2001 | Shinmoto et al. | |
| 6,299,769 B1 | 10/2001 | Falkvall et al. | |
| 6,306,836 B1 | 10/2001 | Martis et al. | |
| 6,309,673 B1 | 10/2001 | Duponchell et al. | |
| 6,605,214 B1 * | 8/2003 | Taylor ........................ | 210/232 |
| 6,623,709 B2 * | 9/2003 | Taylor ........................ | 422/261 |
| 6,676,632 B2 * | 1/2004 | Taylor ........................ | 604/80 |
| 2002/0112609 A1 | 8/2002 | Wong | |

OTHER PUBLICATIONS

"Centrifugal Artificial Kidney", R. M. Kellogg, IBM Technical Disclosure Bulletin, vol. 14, No. 11, Apr. 1972, pp. 3433–3435.

"Combined Technological–Clinical Approach To Wearable Dialysis", Robert L. Stephen et al., Kidney International, vol. 13, Suppl. 8 (1978), pp. S–125–S–132.

"Development of Continuous Recirculating Peritoneal Dialysis Using a Double Lumen Catheter", Michio Mineshima et al., ASAIO Journal, 1992, pp. M377–M381.

"Important Devices in Biomedical Engineering", John G. Webster, International Biomedical Engineering Days, 1992, pp. 1–9.

"Recirculation Peritoneal Dialysis with Sorbent Redy Cartridge", Rasib M. Raja et al., Nephron 16, (1976), pp. 134–142.

"Recirculating Peritoneal Dialysis with Subcutaneous Catheter", R. L. Stephen et al., American Society For Artificial Internal Organs, vol. XXII, 1976, pp. 575–584.

"Sorbent Based Regenerating Delivery System For Use In Peritoneal Dialysis", A. J. Lewin et al., vol. XX Trans. Amer. Soc. Artif. Int. Organs, 1974, pp. 130–134.

"The Use of Reciprocating Peritoneal Dialysis with a Subcuntaneous Peritoneal Catheter in End–Stage Renal Failure in Diabetes Mellitus", G. D. Warden et al., Journal of Surgical Research, vol. 24, Jun. 1978, pp. 495–500.

"Blood Flow and Pressure Measurement", IBM Technical Disclosure Bulletin, Feb. 1971.

"Continuous Flow Dialyzer", IBM Technical Disclosure Bulletin, Jul. 1975.

"Reciprocating Peritoneal Dialysis", Carl Kablitz, M.D. et al., Dialysis & Transplantation, vol. 7, No. 3, Mar. 1978, pp. 211–212 and 214.

"Reciprocating Peritoneal Dialysis with a Subcuntaneous Peritoneal Catheter", Robert L. Stephen, M.D., Dialysis & Transplantation, vol. 7, No. 8, Aug. 1978.

"Studies on low–cost Disposable Bioreactor for Bilirubin Detoxification", B. Das et al., Proceedings RC IEEE–EMBS & 14$^{th}$ BMESI, 1995, 4.53–4.54.

"Technological Augmentation of Peritoneal Urea Clearance: Past, Present, and Future", Carl Kablitz, M.D. et al., Dialysis & Transplantation, vol. 8, No. 8, Aug. 1960, pp. 741–744 and 778.

E–mail–(1995) D. Halligan, "The Human and Artificial Kidney" from Google Search.

"A Membrane System to Remove Urea from the Dialyzing Fluid of the Artificial Kidney" Kolff, W. J. et al., Annual rept. No. 2, Jul. 1, 1978–Jun. 30, 1979).

"The Regenerative Dialysis (REDY) Sorbent System" Roberts M., Nephrology, 1998, V4, N4 (Aug), P275–278.

"In search of a 24 Hours Per Day Artificial Kidney" Lande A. J. et al., Journal of dialysis (U.S.) 1977, 1 (8) p. 805–23, ISSN 0362–8558.

"Efficacy of Lumbo–Peritoneal Versus Ventriculo–Peritoneal Shunting for Management of Chronic Hydrocephalus Following Aneurysmal Subarachnoid Haemorrhage" Kang S., Acta Neurochirurgica, 142 (1):p. 45–49 2000.

"Performance of the Dialytic Reactor with Product Inhibited Enzyme Reactions: A Model Study" Catapano Gerardo et al., Bioseparation 4 (3):p. 201–211 1994.

"Carbonato–Compounds of Zirconium" Russian Journal of Inorganic Chemistry, vol. 11, No. 8, Aug. 1996, pp. 995–1004.

International Search Report for PCT/US01/44623.

Copy of U.S. Appl. No. 09/723,396.

Copy of U.S. Appl. No. 09/996,505.

International Search Report for PCT/US02/35783.

"Sorbent Dialysis Primer," COBE Renal Care, Inc. Sep. 4, 1993 edition.

"Rx Guide to Custom Dialysis," COBE Renal Care, Inc. Revision E, Sep., 1993.

* cited by examiner

FILTER CARTRIDGE ASSEMBLIES AND METHODS FOR FILTERING FLUIDS

FIELD OF THE INVENTION

The present invention relates to filter cartridges and methods for filtering fluids.

BACKGROUND OF THE INVENTION

Filter cartridges are used in many applications, including medical devices. In the medical field, filter cartridges containing certain powdered filter media are used. One application for such a filter cartridge is in a dialysis system.

Systems for patients requiring hemodialysis or peritoneal dialysis can involve pumping a large volume of dialysate through a dialyzing device. In these devices, the used dialysate is generally discarded after a single passing.

More recent embodiments of dialysis devices involve pumping a fixed volume of dialysate through a dialyzing device, whereupon the used dialysate flows through a filter cartridge and is then returned to a dialysate reservoir for reuse. Flow through the cartridge, however, does not optimize filtering of the dialysate through various granular filtering media.

Fluid flows through filter media of varying particle sizes and granular diameters at various rates and pressures. Fluid flows at a higher rate and at a lower pressure through granules of larger diameter. Conversely, fluid flows at a slower rate and at a higher pressure through granules of smaller diameter. The flow of a fluid through a filter cartridge having filter media sections of varying granule diameters takes different directional flow paths through the respective sections. As a result, fluid flow through a powdered medium containing large diameter granules disposed in a filter cartridge is laminar. Fluid flow through a powdered filter medium containing small diameter granules disposed in a filter cartridge is not laminar and results in a condition known as wicking. Wicking occurs when the fluid generally flows in the direction of areas of least pressure which tend to be areas between the inner wall of the tubular housing and the powdered filter medium. Wicking results in the fluid bypassing the majority of the surface area of the granular filter medium. As a result, filtering is inefficient.

A need therefore exists for a filter cartridge assembly that optimizes filtering efficiency of a fluid.

SUMMARY OF THE INVENTION

According to an embodiment of the present invention, a filter cartridge assembly is provided that includes a tubular housing having an inner wall, an outer wall, a first end, a second end, and shoulders between sections of the housing. The shoulders focus the flow of fluid through filter media disposed in the cartridge. A first connector is adapted to seal the first end except at an entrance port where fluid can enter the cartridge. A second connector is adapted to seal the second end except at an exit port where fluid can exit the cartridge. Preferably, the tubular housing has at least three sections wherein the sections have progressively smaller average inner diameters in a direction from the first end to the second end of the tubular housing, and filter media sections traverse two or more shoulders at the intersections of the tubular housing sections.

According to another embodiment of the present invention, a filter cartridge assembly of generally conical shape is provided that includes a tubular housing having an inner wall, a first end, a second end, and a plurality of annular flow deflectors that extend radially inwardly from the inner wall of the tubular housing to focus the flow of fluid through the center of the filter media in the cartridge. The inner wall of the tubular housing is continuously tapering in a direction from the first end of the tubular housing to the second end of the tubular housing. A first connector is adapted to seal the first end except at an entrance port where fluid can enter the filter cartridge. A second connector is adapted to seal the second end except at an exit port where fluid can exit the filter cartridge.

According to yet another embodiment of the present invention, a filter cartridge assembly of generally cylindrical shape is provided that includes a tubular housing having an inner wall, a first end, a second end, and a plurality of annular flow deflectors that extend radially inwardly from the inner wall of the tubular housing to focus the flow of fluid through the center of the filter media in the cartridge. The inner wall is of constant diameter. A first connector is adapted to seal the first end except at an entrance port where fluid can enter the filter cartridge. A second connector is adapted to seal the second end except at an exit port where fluid can exit the filter cartridge.

Powdered filter media for performing many different filtering functions can be used. The different media can cause different reactions, including enzymatic decomposition, cation exchange, anion exchange, or chemical adsorption. The various filter media can consist of different sized and shaped granular or powdered insoluble chemicals that have different physical and chemical characteristics.

According to methods of the present invention, a filter cartridge assembly is provided according to any one of the embodiments listed herein, and a fluid is flowed through or circulated through the filter cartridge by a fluid circulating device, a pump, gravity, or a gravity column.

DETAILED DESCRIPTION OF THE PRESENT INVENTION

Figure 1:
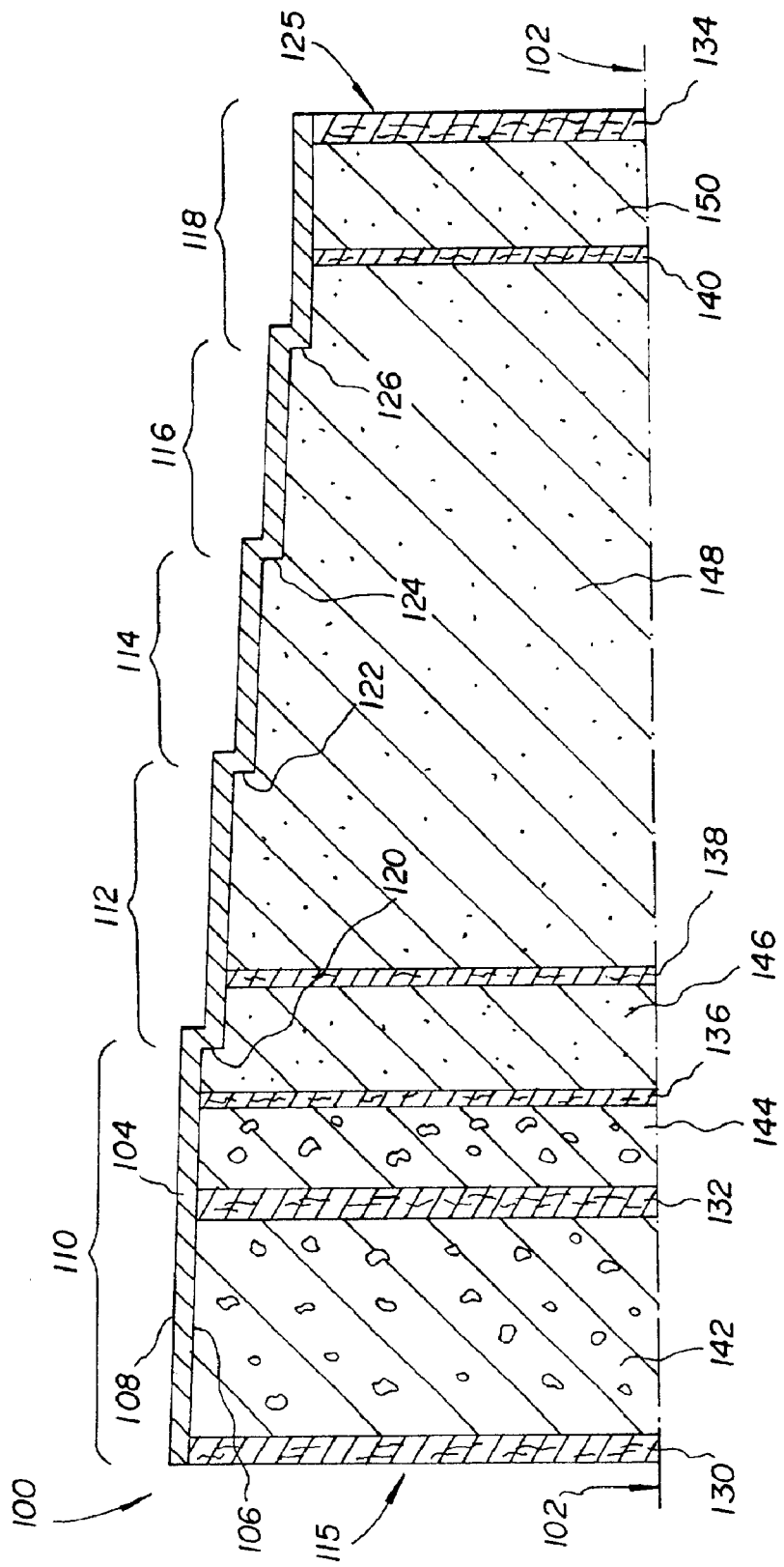
FIG. 1 is a cross-sectional view of half of a filter cartridge according to an embodiment of the present invention wherein the tubular housing has five sections, each successive section has a smaller average inner diameter than the preceding section, and the inner wall of the tubular housing has stepped portions or shoulders at the intersection between each section of the housing.

The present invention overcomes the problems of the prior art by providing a filter cartridge assembly of simple construction and that efficiently filters fluids. The filter cartridge assembly of the present invention can advantageously be less costly to manufacture than conventional filter cartridges and can be employed in recirculating systems. The filter cartridge assembly of the present invention is also less costly to use than conventional filter cartridges because it is more efficient at filtering fluid per unit volume of filter media.

The present invention is also directed to filter cartridge assemblies including various powdered filtered media contained therein. The various powdered filter media can include those media described in U.S. patent application Ser. No. 09/996,505 to Wong, filed concurrently with the present application and entitled "Cartridges Useful in Cleaning Dialysis Solutions". The aforementioned patent application and all other patents and publications mentioned herein are incorporated in their entireties by reference herein.

According to an embodiment of the present invention, a filter cartridge assembly is provided that includes a tubular housing having an inner wall, a first end, a second end, and at least three sections having progressively smaller average inner diameters in a direction from the first end to the second end. A first connector is adapted to seal the first end except at an entrance port where fluid can enter the cartridge. A second connector is adapted to seal the second end except at an exit port where fluid can exit the cartridge. The inner wall of the tubular housing is provided with shoulders at the intersections of the respective sections. The shoulders deflect the flow of fluid from the outer periphery of the filter media to paths that flow through the center of the filter media.

According to another embodiment of the present invention, a filter cartridge assembly of conical shape is provided that includes a tubular housing having an inner wall, a first end, a second end, and a plurality of annular flow deflectors that extend radially inwardly from the inner wall of the tubular housing. By conical what is meant is generally conical, preferably perfectly conical, and more preferably having a continuously decreasing inner diameter defined by the inner wall regardless of the shape of the outside of the filter cartridge. The annular flow deflectors can be integrally formed or molded with the inner wall of the tubular housing or attached, mounted, fixed, or positioned on the inner wall of the tubular housing by a compression fit, threaded engagement, by snapping in a groove, or by other means. For example, adhesive well known to those of ordinary skill in the art can be used to affix the annular flow deflectors to the inner wall. For another example, the annular flow deflector can be held in place by filter media in a tightly packed, compressed, or settled form. A first connector is adapted to seal the first end except at an entrance port where fluid can enter the filter cartridge. A second connector is adapted to seal the second end except at an exit port where fluid can exit the filter cartridge. The inner wall of the tubular housing is continuously tapering in a direction from the first end to the second end.

According to yet another embodiment of the present invention, a filter cartridge assembly having a cylindrical shape is provided that includes a tubular housing having an inner wall, a first end, a second end, and a plurality of annular flow deflectors that extend radially inwardly from the inner wall. By cylindrical, what is meant is generally cylindrical, preferably perfectly cylindrical, more preferably having a constant inner diameter defined by the inner wall regardless of the shape of the outside of the filter cartridge. The annular flow deflectors can be integrally formed or molded with the inner wall of the tubular housing or attached, mounted, fixed, or positioned on the inner wall of the tubular housing by a compression fit, threaded engagement, by snapping in a groove or by other means. For example, adhesive well known to those of ordinary skill in the art can be used to affix the annular flow deflectors to the inner wall. For another example, the annular flow deflector can be held in place by filter media in a tightly packed, compressed, or settled form. A first connector is adapted to seal the first end except at an entrance port where fluid can enter the filter cartridge. A second connector is adapted to seal the second end except at an exit port where fluid can exit the filter cartridge.

According to methods of the present invention, any of the filter cartridge assemblies of the present invention can be used in a recirculating system to filter a recirculating fluid.

The diameter of the inner wall of the tubular housing can be modulated to regulate pressure and the flow rate. The diameter of the inner wall, for example, from about 4 to about 7 inches, can result in a flow rate of, for example, from about 150 ml/min to about 500 ml/min at a pressure of less than or equal to, for example, about 25 pounds per square inch.

Some filter media, for example, activated carbon, have relatively large granules (coarse media), for example, with diameters of from about 425 micrometers to about 1,700 micrometers. Some filter media, for example, zirconium phosphate or alumina, have relatively small granules (fine media), for example, having diameters of from about 20 micrometers to about 100 micrometers, e.g. from about 45 micrometers to about 100 micrometers.

It is a feature of this invention that laminar flow of fluid through the tubular housing of the filter cartridge apparatus is maintained. Annular flow deflectors are used to ensure laminar flow of the fluid through fine filter media. Pumping the fluid against the force of gravity, for example, by standing the assembly on end, is further used to maintain laminar flow of the fluid through the tubular housing.

Experiments show that the flow of fluid through a conventional filter cartridge containing a fine medium can result in wicking and non-laminar flow. Wicking occurs when the flow of fluid is generally directed toward the inner wall to an area of least resistance and pressure between the inner wall and the filter medium. Therefore, the fluid does not contact a substantial portion of the surface area of the total filter medium, resulting in low utilization of the filter medium. In the filter cartridge of the present invention, the annular flow deflectors deflect the flow of fluid through filter medium, particularly through fine medium. The fluid contacts substantially all of the surface area of the fine filter medium, resulting in high utilization of the filter medium.

It is a feature of this invention that only a low percentage of the fluid bypasses a section of the filter media, for example, less than 20 percent bypasses the filter media of each, more preferably less than 10 percent, and even more preferably less than 3 percent bypasses the filter media of each section. Preferably, the annular flow deflectors are attached to the inner wall of the tubular housing within a section of a filter medium.

The extent that the annular flow deflector extends into the housing from the inner wall is preferably from about 1.0 percent to 5.0 percent of the diameter of the inner wall at the flow deflector. If the width of the concentric surface of the annular flow deflector is too great, utilization of the filter medium behind the annular flow deflector is lower than the average utilization of the filter medium. If the width of the concentric surface of the annular flow deflector is too little, deflection of the fluid may not result in laminar flow and wicking occurs.

An embodiment of the present invention includes a first connector and a second connector adapted to seal the first end and the second end, respectively. The first connector and the second connector can be hermetically sealed to the first end and the second end using, for example, a variety of conventional sealing techniques, such as, but not limited to, EMABOND, Ashland Specialty Chemical Company, a division of Ashland, Inc., Columbus, Ohio, or another sealing composition or method such as ultrasound, heat, chemical bonding, vibration, physical latch, or gasket. The sealing method preferably is capable of withstanding moderate pressures of greater than 40 pounds per square inch.

In another embodiment of the present invention, the entrance port and exit port of the filter cartridge assembly are connected to a fluid recirculating or pumping system. The fluid recirculating system can be, for example, a dialysis machine, including a portable dialysis machine. The fluid recirculating system can include, for example, a fluid pump, a dialyzing device, and a fluid reservoir.

According to an embodiment of the present invention, methods of preparing an assembly according to the present invention are provided wherein a filter medium seal is inserted into one of the first end and the second end of the tubular housing. The filter medium seal or part thereof can be a filter paper, a filter pad, a first connector, and a second connector. Many seals can be used. Each filter medium seal is preferably disk-shaped and preferably has an outer periphery that matches the inner periphery of the tubular housing at the location of the seal within the tubular body. After the seal is inserted, a filter medium is introduced into the tubular housing to form a part of or an entire filter medium section, and the filter medium is subsequently settled as by vibrating, packing, shaking, jogging, compressing, or otherwise increasing the density of the filter medium section. Following settling and optional additional placement of at least one seal in the tubular body, the other of the first and second ends of the tubular housing is sealed with another filter medium seal to contain the filter medium section and maintain the density of the filter medium section.

Figure 4:
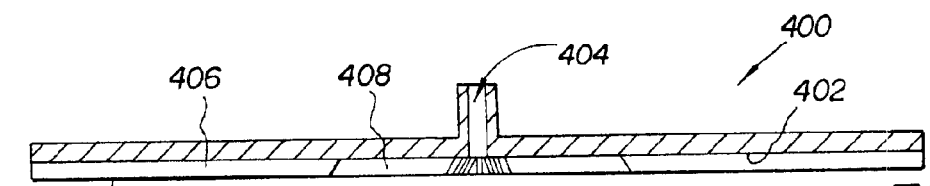
FIG. 4 is a cross-sectional side view of an end cap or connector useful with the filter cartridges of the present invention.
Figure 5:
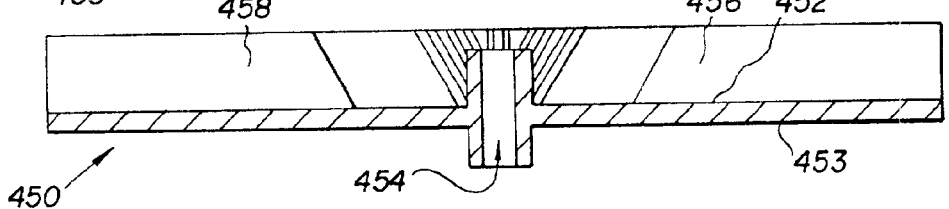
FIG. 5 is a cross-sectional side view of an end cap or connector useful with the filter cartridge of the present invention.
Figure 6:
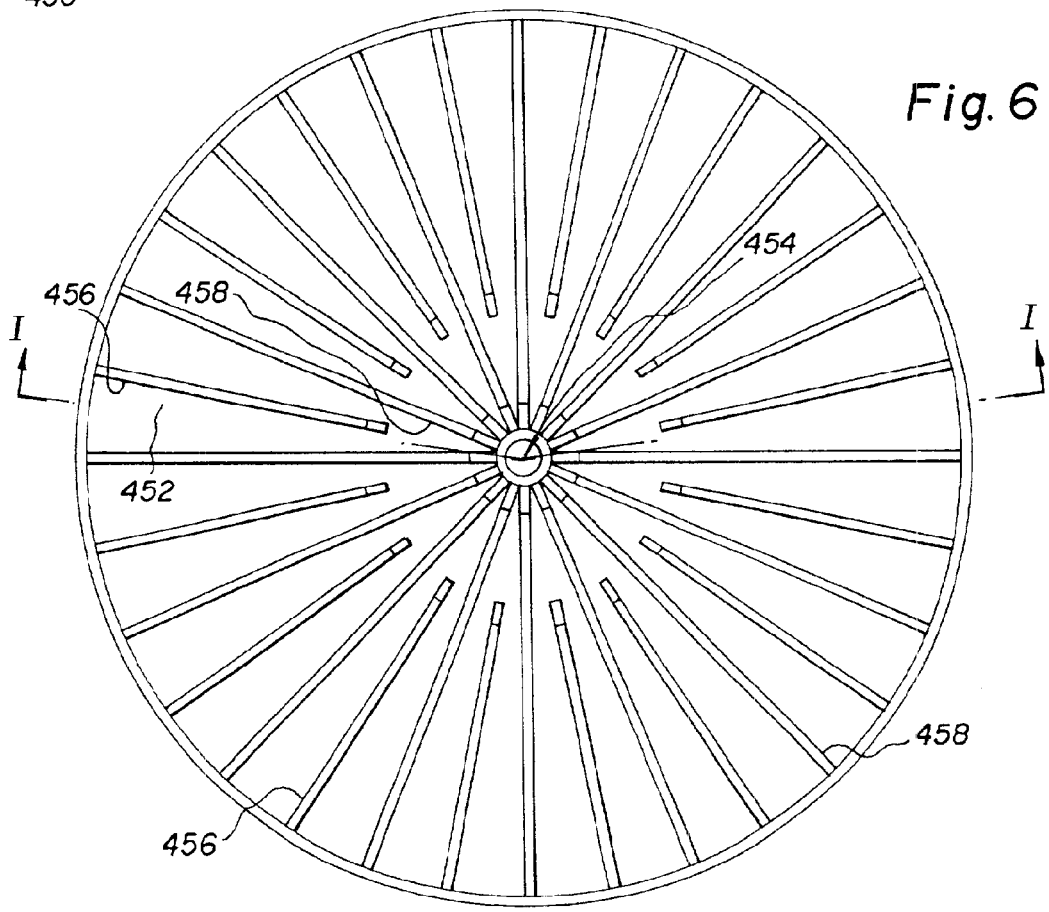
FIG. 6 is an end view of the inner surface of the connector shown in FIG. 5.

Referring now to the figures, FIG. 1 is a cross-sectional view of half of a filter cartridge assembly 100 according to an embodiment of the present invention, wherein the end connectors are removed. The other half of the cartridge cross-section (not shown) is a mirror image of the cartridge half cross-section shown, along centerline 102 of FIG. 1. The cartridge 100 includes a tubular housing 104 having an inner wall 106 and an outer wall 108. The tubular housing 104 has, by way of example, five sections 110, 112, 114, 116, and 118. The sections have lengths having progressively smaller average inner diameters in a direction from a first end 115 to a second end 125 of the tubular housing 104. The inner wall 106 of the tubular housing 104 is provided with shoulders 120, 122, 124, and 126 at the intersections between the respective adjacent sections of the tubular housing. Each shoulder acts as an annular flow deflector extending radially inwardly from the inner wall 106. A first end cap or connector (not shown) is adapted to seal the first end 115 of the cartridge 100 except at an entrance port where fluid can enter the cartridge. A second end cap or connector (not shown) is adapted to seal the second end 125 except at an exit port where fluid can exit the cartridge. Details of the first and second connectors are shown in FIGS. 4–6.

Sections of various filter media are contained within the tubular housing 104. Preferably, at least one filter medium section spans portions of at least two lengths of inner wall sections 110, 112, 114, 116, and 118 such that the filter medium section traverses a shoulder 120, 122, 124, or 126. Thick, porous filter pads 130, 132, and 134 can be used to contain filter media within the tubular housing 104 or can be used to maintain separation between two adjacent filter media sections, for example, between granular filter media sections having different and widely disparate average granule diameters. Thinner, porous filter paper 136, 138, and 140 can be used, for example, to maintain separation between two adjacent granular filter media sections having similar average granule diameters. The filter pads 130, 132, and 134, and the filter papers 136, 138, and 140, are each preferably disk-shaped and each preferably has an outer periphery that matches the inner periphery of the tubular housing 104 at the location of the respective pad or paper within the tubular housing 104.

For example purposes only, the various filter media sections within the tubular housing 104 can include, as shown, a granular activated carbon section 142, an immobilized enzyme section 144, a powdered alumina ($Al_2O_3$) section 146, a zirconium phosphate section 148, and a section 150 that includes a mixture of hydrous zirconium oxide of the acetate form and sodium zirconium carbonate.

Figure 2:
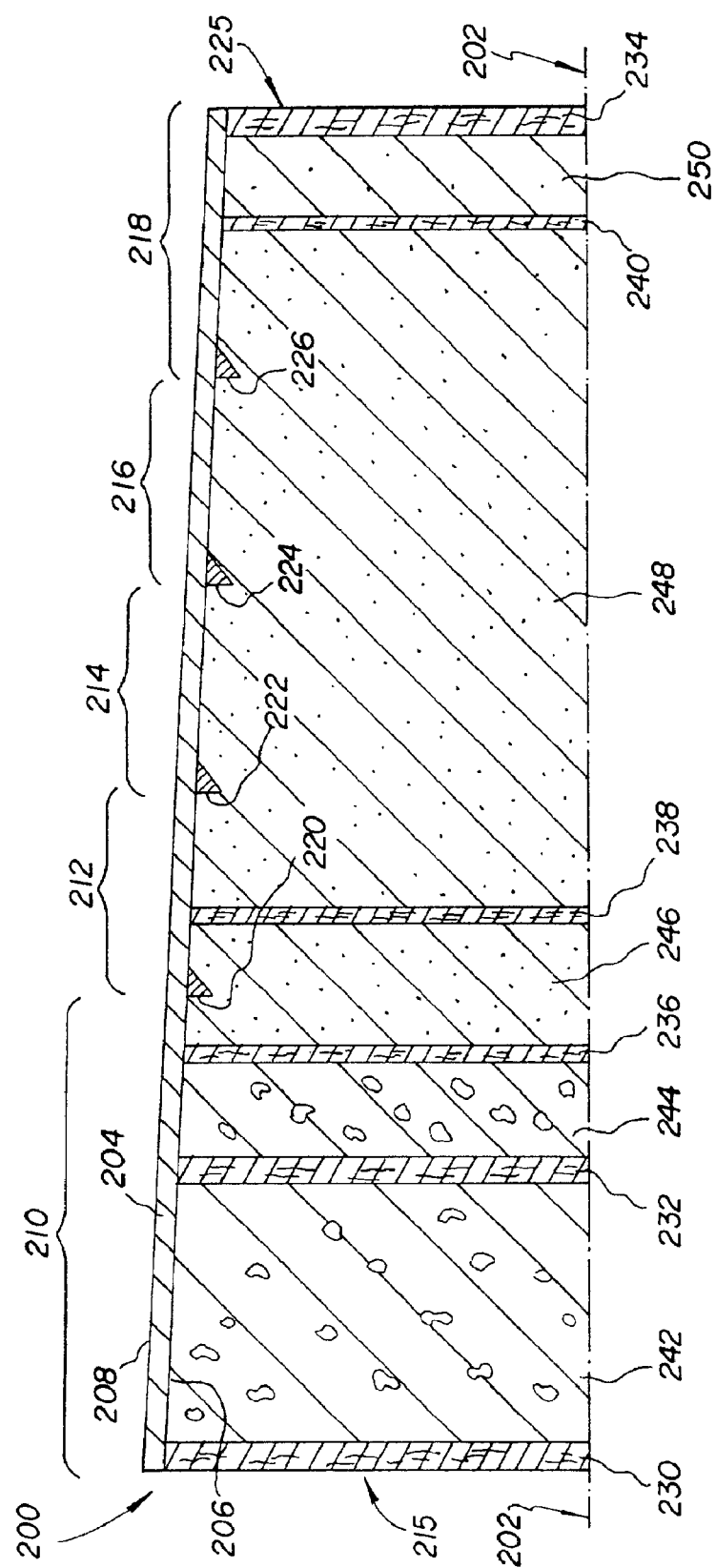
FIG. 2 is a cross-sectional view of half of a filter cartridge according to an embodiment of the present invention wherein the diameter of the inner wall of the tubular housing continuously tapers from the direction of a first end to a second end of the housing.

FIG. 2 is a cross-sectional view of half of a filter cartridge 200 according to another embodiment of the present invention, wherein the end connectors are removed. The other half of the cartridge cross-section (not shown) is a mirror image of the cartridge half cross-section shown, along centerline 202 of FIG. 2. The cartridge 200 includes a tubular housing 204 having an inner wall 206 and an outer wall 208. The tubular housing 204 has, by way of example, five sections 210, 212, 214, 216, and 218. The sections 210, 212, 214, 216, and 218 have lengths having an average inner diameter defined by the inner wall 206, that continuously tapers in a direction from a first end 215 to a second end 225 of the tubular housing 204.

Annular flow deflectors 220, 222, 224, and 226 extend radially inwardly from the inner wall 206. The annular flow deflectors 220, 222, 224, and 226 are positioned within the tubular housing 204 and held in place adjacent to the inner wall 206 by the compression of the powdered filter media sections. After filter media is inserted and packed into the tubular housing 204, the annular flow deflectors 220, 222, 224, and 226 are held in a stationary position by compression of the surrounding filter media. The concentric surface of the annular flow deflectors 220, 222, 224, and 226 can have a width equal to approximately 1.0 to 5.0 percent of the diameter of the inner wall 206 of the tubular housing 204. A first end cap or connector (not shown) is adapted to seal the first end 215 of the cartridge 200 except at an entrance port where fluid can enter the cartridge. A second end cap or connector (not shown) is adapted to seal the second end 225 except at an exit port where fluid can exit the cartridge. Details of the first and second connectors are shown in FIGS. 4–6.

Sections of various filter media are contained within the tubular housing 204. Preferably, at least one filter medium section spans portions of at least two lengths of inner wall sections 210, 212, 214, 216, and 218 such that the filter medium section traverses an annular flow deflector 220, 222, 224, or 226. Thick, porous filter pads 230, 232, and 234 can be used to contain filter media within the tubular housing 204 or can be used to maintain separation between two adjacent filter media sections, for example, between granular filter media sections having different and widely disparate average granule diameters. A thick filter pad can be used at the respective intersection of each two adjacent sections of filter media. Thinner, porous filter paper 236, 238, and 240 can be used, in addition to the thick filter pads, or as an alternative to the thick filter pads, for example, to maintain separation between two adjacent granular filter media sections having similar average granule diameters. The filter pads 230, 232, and 234, and the filter papers 236, 238, and 240, are each preferably disk-shaped and each preferably has an outer periphery that matches the inner periphery of the tubular housing 204 at the location of the pad or paper within the tubular housing 204.

The various filter media sections within the tubular housing 204 can include, as shown, a granular activated carbon section 242, an immobilized enzyme section 244, a powdered alumina ($Al_2O_3$) section 246, a zirconium phosphate section 248, and a section 250 that includes a mixture of hydrous zirconium oxide of the acetate form and sodium zirconium carbonate.

Figure 3:
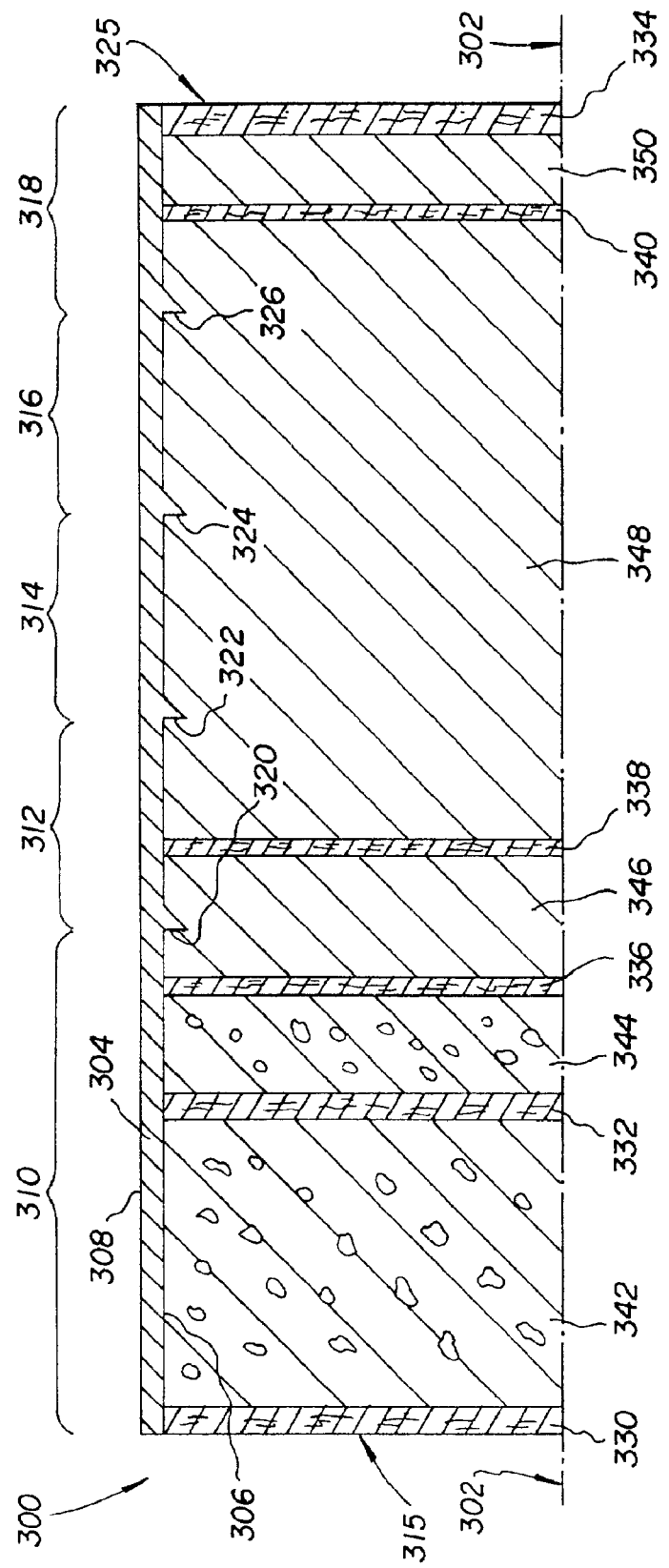
FIG. 3 is a cross-sectional view of half of a filter cartridge according to yet another embodiment of the present invention wherein annular flow deflectors are positioned on the inner wall of a cylindrical tubular housing.

FIG. 3 is a cross-sectional view of half of a filter cartridge 300 according to yet another embodiment of the present invention, wherein the end connectors are removed. The other half of the cartridge cross-section (not shown) is a mirror image of the cartridge half cross-section shown, along centerline 302 of FIG. 3. The cartridge 300 includes a tubular housing 304 having an inner wall 306 and an outer wall 308. The tubular housing 304 has, by way of example, five sections 310, 312, 314, 316, and 318. The sections 310, 312, 314, 316, and 318 have lengths having an inner diameter defined by the inner wall 306, that is constant from a first end 315 to a second end 325 of the tubular housing 304.

Annular flow deflectors 320, 322, 324, and 326 extend radially inwardly from the inner wall 306. The annular flow deflectors 320, 322, 324, and 326 are integrally molded with the inner wall 306 of the tubular housing 304. The concentric surface of the annular flow deflectors 320, 322, 324, and 326 can have a width equal to approximately 1.0 to 5.0 percent of the diameter of the inner wall 306 of the tubular housing 304. A first end cap or connector (not shown) is adapted to seal the first end 315 of the cartridge 300 except at an entrance port where fluid can enter the cartridge. A second end cap or connector (not shown) is adapted to seal the second end 325 except at an exit port where fluid can exit the cartridge. Details of the first and second connectors are shown in FIGS. 4–6.

Sections of various filter media are contained within the tubular housing 304. Preferably, at least one filter medium section spans portions of at lest two lengths of inner wall sections 31, 312, 314, 316, and 318 such that the filter medium section traverses an annular flow deflector 320, 322, 324, or 326. Thick, porous filter pads 330, 332, and 334 can be used to contain filter media within the tubular housing 304 or can be used to maintain separation between two adjacent filter media sections, for example, between granular filter media sections having different and widely disparate average granule diameters. Thinner, porous filter paper 336, 338, and 340 can be used, for example, to maintain separation between two adjacent granular filter media sections having similar average granule diameters. The filter pads 330, 332, and 334, and the filter papers 336, 338, and 340, are each preferably disk-shaped and each preferably has an outer periphery that matches the inner periphery of the tubular housing 304 at the location of the pad or paper within the tubular housing 304.

The various filter media sections within the tubular housing can include any of a variety of filter media materials and combinations thereof. By way of example, the figures depict filter media sections that can include, as shown, a granular activated carbon section 342, an immobilized enzyme section 344, a powdered alumina ($Al_2O_3$) section 346, a zirconium phosphate section 348, and a section 350 that includes a mixture of hydrous zirconium oxide of the acetate form and sodium zirconium carbonate.

The various filter media shown in FIGS. 1–3 are for example only and in no way limit the filter media used or the order in which the filter media can be disposed with respect to the direction of flow of the fluid.

Activated carbon can be used as a filter medium to bind heavy metals, oxidants, and chloramines. An immobilized enzyme such as urease can be used in a filter medium to convert urea to ammonium carbonate by enzymatic conversion. Urease can be immobilized by adsorption, covalent bonding, intermolecular cross-linking, entrapment within cross-linked polymers, microencapsulation, and containment within a semipermeable membrane device. Alumina ($Al_2O_3$), activated carbon, anion exchange resins, and diatomaceous earth can be used as adsorbents. Urease can be used to covalently bond water-insoluble polymers to form enzyme-polymer conjugates via activation procedures or reactive polymers. Multifunctional reagents, for example, glutaraldehyde and hexamethylene diamine can be used to affect intermolecular cross-linking of urease. Urease can be entrapped within a cross-linked polymer, such as, for example, polyacrylamide gel. Urease can be microencapsulated using, for example, nylon, cellulose nitrate, ethyl cellulose, or polyamide. Urease can be contained within some permeable membrane device, such as, for example, AMICOM ultra-filtration cells, available from Fisher Scientific, Pittsburgh, Pa., or DOW hollow fiber beaker device, from The Dow Chemical Co., Midland, Mich. The use of activated carbon to remove chlorine, if used, should precede the immobilized enzyme medium because chlorine can deactivate the enzyme.

Cation exchange materials can be used to bind ammonium, calcium, magnesium, potassium, and other cations as well as toxic trace metals in tap water. Another function of these filter media can be to convert carbonate from urea hydrolysis to bicarbonate. Such cation exchange materials can include zirconium phosphate, titanium phosphate, or zeolite.

Anion exchange filter media bind phosphate, fluoride, and other heavy metals. Bi-products of the anion exchange filter media can include acetate and bicarbonate, which also corrects for metabolic acidosis of a patient's blood. Such filter media can include hydrous zirconium oxide of the acetate form, hydrous silica, stannic oxide, titanium oxide, antimonic acid, hydrous tungsten oxide, or sodium zirconium carbonate.

For hemodialysis, a filter medium adapted to remove chlorine from tap water is preferred unless highly purified water is used as a base for the dialysate. The medium can be activated carbon.

The cation exchange filter medium, for example, zirconium phosphate, as shown in FIGS. 1–3, includes a section wherein flow deflectors 122, 124, and 126 (FIG. 1), 222, 224, and 226 (FIG. 2), and 322, 324, and 326 (FIG. 3), are provided between the first end of the cation exchange filter medium section and the second end of the cation exchange filter medium section. Preferably, at least one annular flow deflector is provided at about the midway point of the cation exchange filter medium section.

FIG. 4 is a cross-sectional view of a second connector 400 adapted to seal the second end of the tubular housing (not shown). The connector 400 has an inner side 402, an outer side 403, an exit port 404, and radially extending ribs or guide vanes 406 and 408, such that the inner side 402 intersects the inner wall of the tubular housing (not shown) when sealed on the housing. The radially extending ribs 406 extend from an outer periphery of the inner side 402 inward toward the exit port 404 and approach, but do not contact the exit port 404. The radially extending ribs 408 extend from an outer periphery of the inner side 402 inward toward the exit port 404 and terminate immediately adjacent the exit port 404. As the flow of a fluid reaches the second end of the tubular housing (not shown) from the direction of the first end of the tubular housing (not shown), the fluid is directed radially inward to the exit port 404 by the radially extending ribs 406 and 408.

FIG. 5 is a cross-sectional view of a first connector 450 of FIG. 6 cut through line I—I and adapted to seal the first end of the tubular housing (not shown). The connector 450 has an inner side 452, an outer side 453, an entrance port 454, and radially extending ribs or guide vanes 456 and 458, such that the inner side 452 intersects the inner wall of the tubular housing (not shown) when sealed on the housing. The radially extending ribs 456 extend from an outer periphery of the inner side 452 inward toward the entrance port 454 and approach, but do not contact the entrance port 454. The radially extending ribs 458 extend from an outer periphery of the inner side 452 inward toward the entrance port 454 and terminate immediately adjacent the entrance port 454. As the flow of a fluid enters the first end of the tubular housing (not shown) through the entrance port 454, the fluid is directed radially outward from the entrance port 454 by the radially extending ribs 456 and 458.

FIG. 6 is a top view of the first connector 450 and illustrates an exemplary embodiment of the radially extending ribs 456 and 458, the entrance port 454, and the inner side 452.

Figure 7:
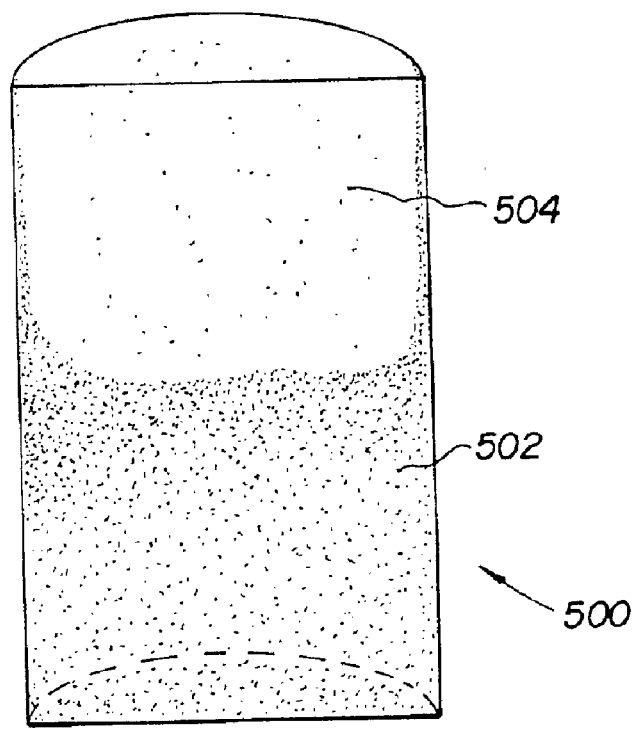
FIG. 7 is an illustration of a cross-section of the filter medium following filtration of a fixed volume of fluid in a conventional filter cartridge apparatus.

FIG. 7 is a diagram of a cross section of the filter medium 500 in a conventional filter cartridge apparatus following filtration of a fixed volume of fluid. The cross section is representative of filter medium taken from a tubular housing wherein the diameter of the inner wall of the tubular housing remains constant in a direction from a first end (bottom end) of the tubular housing to a second end (top end) of the tubular housing. The cross-section is also representative of a filter medium taken from a section of a tubular housing wherein the section has a continuous average inner diameter.

The gray area 502 shown in FIG. 7 illustrates the flow of fluid through a zirconium phosphate filter medium. The white area 504 illustrates the area of zirconium phosphate filter medium through which the fluid has not flowed. Wicking is evident at the intersection of the white and gray areas in regions adjacent the inner wall of the tubular housing. Experimental results show that approximately 50 percent of the filter medium in such a design may not be utilized.

Figure 8:
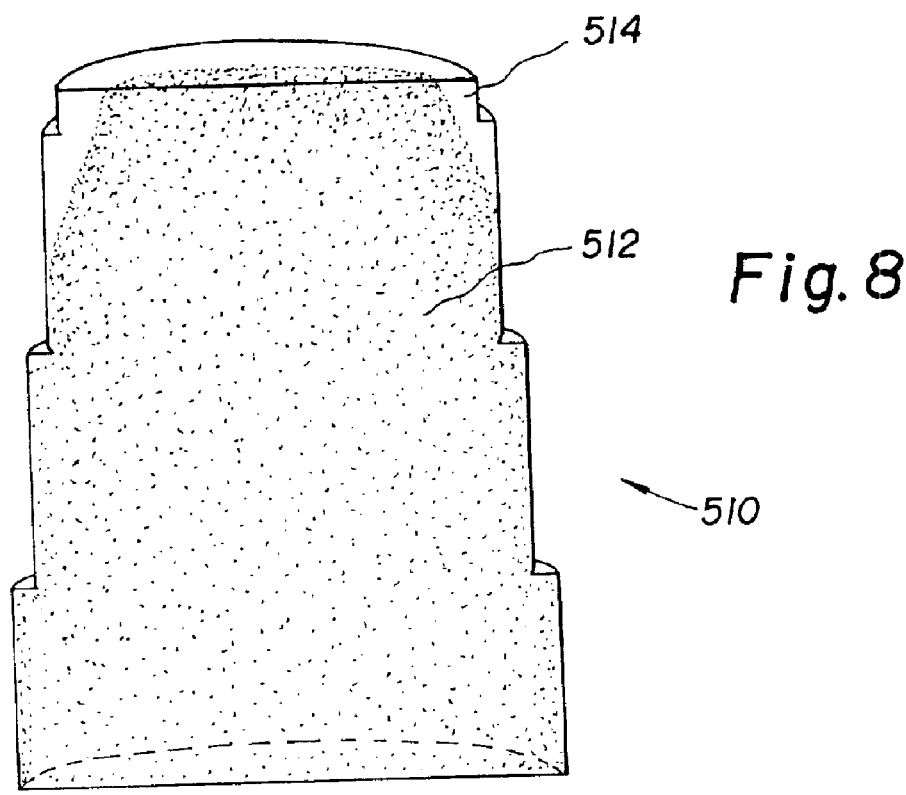
FIG. 8 is an illustration of a cross-section of a zirconium phosphate filter medium following filtration of a fixed volume of fluid in a filter cartridge assembly of the present invention.

FIG. 8 is a diagram of a cross-section of zirconium phosphate filter medium 510 following filtration of a fixed volume of fluid through a filter cartridge assembly of the present invention. The cross-section is representative of a tubular housing having four sections. The sections have progressively smaller average inner diameters in a direction from a first end (bottom end) to a second end (top end) of the tubular housing. The inner wall of the tubular housing from which the medium was removed was provided with shoulders defining intersections between the respective sections. The shoulders acted as flow deflectors.

The gray area 512 shown in FIG. 8 illustrates the flow of fluid through zirconium phosphate filter medium. The white area 514 illustrates an area of zirconium phosphate filter medium that has not been utilized to filter the fluid. Experimental results show that the filter medium had a much higher utilization rate than the filter medium from the filter cartridge shown in FIG. 7, 98 percent versus 50 percent, respectively. The experimental results indicate that laminar flow of fluid was substantially maintained throughout the filter medium and wicking did not occur.

Figure 9:
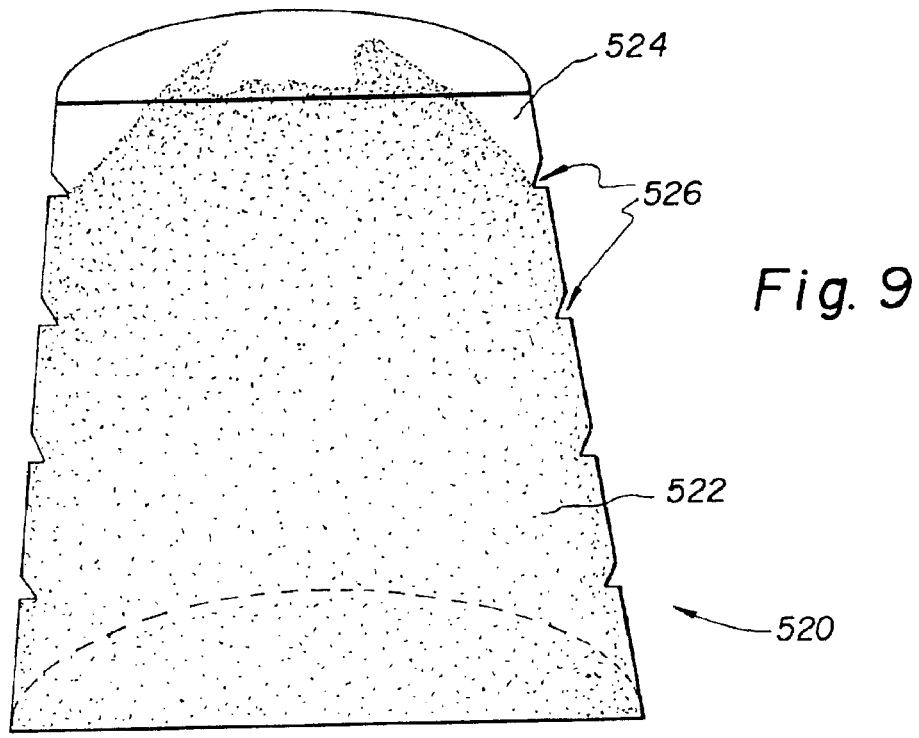
FIG. 9 is an illustration of a cross-section of a zirconium phosphate filter medium following filtration of a fixed volume of fluid in a filter cartridge assembly according to another embodiment of the present invention.

FIG. 9 is a diagram of a cross-section of zirconium phosphate filter medium 520 following filtration of a fixed volume of fluid in a filter cartridge apparatus of the present invention. The cross-section is representative of filter medium removed from a tubular housing having a continuously decreasing inner diameter from a first end (bottom end) of the tubular housing to a second end (top end) of the tubular housing. The indentations 526 approximately perpendicular to the inner wall of the tubular housing result from a molding of the filter medium around the annular flow deflectors on the inner wall of the tubular housing.

The gray area 522 shown in FIG. 9 illustrates the flow of fluid through the zirconium phosphate filter medium. The white area 524 illustrates an area of zirconium phosphate filter medium that has not been utilized to filter the fluid. Experimental results show that the filter medium has a much higher utilization rate than the filter medium used in the filter cartridge shown in FIG. 7, 95 percent versus 50 percent, respectively. The experimental results indicate that laminar flow of the fluid was substantially maintained throughout the filter medium and wicking did not occur.

Figure 10:
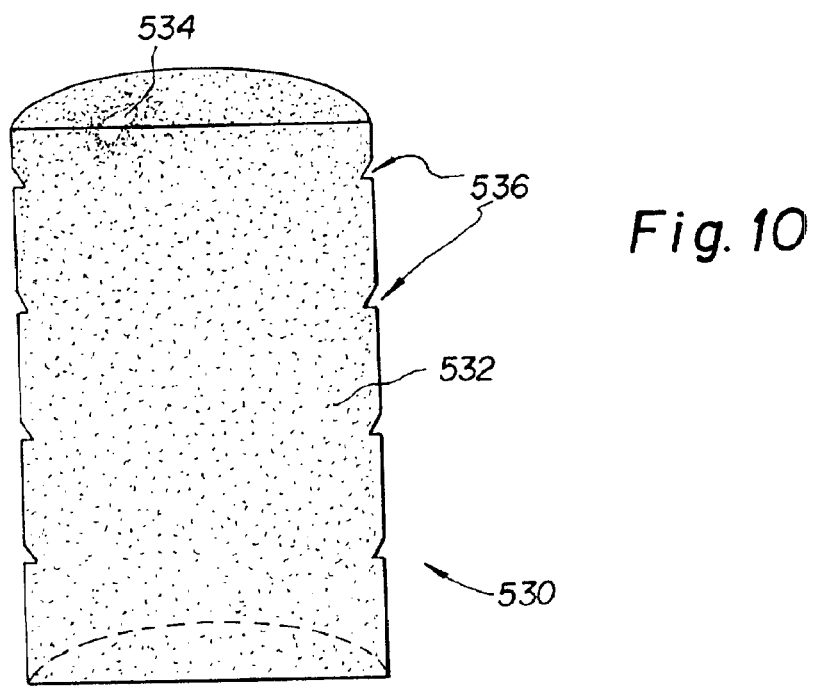
FIG. 10 is an illustration of a cross-section of a zirconium phosphate filter medium following filtration of a fixed volume of fluid in a filter cartridge assembly according to yet another embodiment of the present invention.

FIG. 10 is a diagram of a cross-section of zirconium phosphate filter medium 530 removed from a filter cartridge assembly of the present invention following filtration of a fixed volume of fluid. The cross-section is representative of a tubular housing wherein the tubular housing has a constant inner diameter from a first end (bottom end) of the tubular housing to a second end (top end) of the tubular housing. The indentations 536 perpendicular to the inner wall of the tubular housing result from a molding of the filter medium around the annular flow deflectors on the inner wall of the tubular housing.

The gray area 532 shown in FIG. 10 illustrates the flow of fluid through zirconium phosphate filter medium. The white area 534 illustrates an area of zirconium phosphate filter medium that has not been utilized to filter the fluid. Experimental results show that the filter medium has a much higher utilization rate than the filter medium from the filter cartridge shown in FIG. 7, 99.5 percent versus 50 percent, respectively. The experimental results indicate that laminar flow of the fluid was substantially maintained throughout the filter medium and wicking did not occur.

According to methods of the present invention, a fluid is filtered using an assembly of the present invention. In such methods, a fluid enters the filter cartridge apparatus through an end connector entrance port and is immediately directed radially outwardly by a plurality of radially extending ribs on the inner surface of the connector. The fluid then begins to flow through the filter media within the tubular housing of the assembly. The fluid hydrates the filter media during use. Some filter media may expand to up to 105% of its dry volume. As this occurs, the tubular housing preferably flexes to accommodate the increased volume of the filter media. Uniform, compact, and level packing of each section of the filter media is required to ensure laminar flow of the fluid within the tubular housing.

The inner walls of the tubular housing can include a semi-rigid, thin-walled material, for example, polypropylene or another plastic of similar physical characteristics. The thickness of the wall of the tubular housing is preferably sufficient to ensure structural rigidity and protection during manufacturing, shipping, installation, and use, yet preferably is thin enough to be flexible to accommodate the expansion of the filter media within the tubular housing.

As fluid flows through the assembly and approaches the second end of the tubular housing, the fluid is radially directed inwardly toward the exit port on an end connector by the radially extending ribs on the inner surface of the second connector.

It will be apparent to those skilled in the art that various modifications and variations can be made to the embodiments of the present invention without departing from the spirit or scope of the present invention. Thus, it is intended that the present invention cover other modifications and variations of this invention within the scope of the appended claims and their equivalents.

What is claimed is:

1. A filter cartridge assembly comprising:
   a tubular housing having an inner wall, an outer wall, a first end, and a second end, said inner wall including at least a first section, a second section, and a third section, said first section having a first length in a direction from said first end to said second end and a first average inner diameter, said second section having a second length in a direction from said first end to said second end and a second average inner diameter that is smaller than said first average inner diameter, said third section having a third length in a direction from said first end to said second end and a third average inner diameter that is smaller than said second average inner diameter, wherein the inner wall of said tubular housing includes a first shoulder at the intersection of said first section and said second section and a second shoulder at the intersection of said second section and said third section; and
   a plurality of filter media sections within the tubular housing and radially contained by said inner wall, each of said plurality of filter media sections having a filter media composition, wherein at least one of said plurality of filter media sections has a length in a direction from said first end to said second end that includes at least portions of at least two of said lengths of the inner wall sections such that said at least one of said plurality of media sections traverses at least one of said shoulders.

2. The assembly of claim 1, wherein said assembly further comprises:
   a first connector that seals the first end of said tubular housing except at a centrally-located entrance port in said connector where fluid is capable of entering the assembly; and
   a second connector that seals the second end of said tubular body except at a centrally-located exit port where fluid is capable of exiting the cartridge.

3. The assembly of claim 2, wherein said assembly further contains a dialysate fluid.

4. The assembly of claim 2, wherein said tubular housing comprises a plastic material.

5. The assembly of claim 4, wherein said plastic material comprises a polypropylene material.

6. The assembly of claim 1, wherein the thickness of said inner wall is less than, or equal to, about 0.125 inch.

7. The assembly of claim 1, wherein said at least one of said plurality of filter media sections traverses said first shoulder, wherein at least another one of said plurality of filter media sections includes a different filter media composition than said at least one of said plurality of filter media sections, said at least another one of said plurality of filter media sections has a length in a direction from said first end to said second end that includes at least portions of said second length and said third length of said inner wall sections, and said at least another one of said plurality of filter media sections traverses said second shoulder.

8. A system including the assembly of claim 2, in combination with a fluid circulating device, wherein said device has an outlet and an inlet, said entrance port is in fluid communication with said outlet, and said exit port is in fluid communication with said inlet.

9. A method of filtering a fluid, comprising circulating said fluid through the system of claim 8.

10. A method of preparing tile assembly of claim 2, comprising:
    providing said tubular housing;
    sealing one of said first and second end connectors to said tubular housing;
    introducing a first of said filter media sections into said tubular housing;
    settling said first media section in said tubular housing; and
    sealing the other of said first and second connectors to said tubular body.

11. A filter cartridge housing comprising:
    a tubular housing having a conical shape and including a straight inner wall, an outer wall, a first end, and a second end, said inner wall including at least a first section, a second section, and a third section, said first section having a first length in a direction from said first end to said second end and a first average inner diameter, said second section having a second length in a direction from said first end to said second end and a second average inner diameter that is smaller than said first average inner diameter, said third section having a third length in a direction from said first end to said second end and a third average inner diameter that is smaller than said second average inner diameter; and
    a first annular flow director extending radially inwardly from the inner wall of said tubular housing at the intersection of said first section and said second section, and a second annular flow director extending radially inwardly from the inner wall at the intersection of said second section and said third section.

12. An assembly comprising:

the filter cartridge housing of claim 11; and a plurality of filter media sections within the tubular housing and radially contained by said inner wall, each of said plurality of filter media sections having a filter media composition, wherein at least one of said plurality of filter media sections has a length in a direction from said first end to said second end that includes at least portions of at least two of said lengths of the inner wall sections such that said at least one of said plurality of filter media sections traverses at least one of said first and second annular flow director.

13. The assembly of claim 12, wherein said assembly further comprises:

a first connector that seals the first end of said tubular housing except at a centrally-located entrance port in said connector where fluid is capable of entering the assembly; and a second connector that seals the second end of said tubular body except at a centrally-located exit port where fluid is capable of exiting the cartridge.

14. The assembly of claim 13, wherein said assembly further contains a dialysate fluid.

15. The filter cartridge housing of claim 11, wherein said tubular housing comprises a plastic material.

16. The filter cartridge housing of claim 15, wherein said plastic material comprises a polypropylene material.

17. The filter cartridge housing of claim 1, wherein the thickness of said inner wall is less than, or equal to, about 0.125 inch.

18. The assembly of claim 12, wherein said at least one of said plurality of filter media sections traverses said first annular flow director, wherein at least another one of said plurality of filter media sections includes a filter media composition than said at least one of said plurality of filter media sections, said at least another one of said plurality of filter media sections has a length in a direction from said first end to said second end that includes at least portions of said second length and said third length of said inner wall sections, and said at least another one of said plurality of filter media sections traverses said second annular flow director.

19. A system including the assembly of claim 13, in combination with a fluid circulating device, wherein said device has an outlet and an inlet, said entrance port is in fluid communication with said outlet, and said exit port is in fluid communication with said inlet.

20. A method of filtering a fluid, comprising circulating said fluid through the system of claim 19.

21. A method of preparing the assembly of claim 13, comprising:

providing said tubular housing;

sealing one of said first and second end connectors to said tubular housing;

introducing at least one of said plurality of said filter media sections into said tubular housing;

settling said at least one of said plurality of filter media sections in said tubular housing; and sealing the other of said first and second connectors to said tubular body.

22. A filter cartridge assembly comprising:

a filter cartridge housing including a tubular housing having a cylindrical shape of constant inner diameter and including a straight inner wall, an outer wall, a first end, and a second end, said inner wall including at least a first section, a second section, and a third section, said first section having a first length in a direction from said first end to said second end, said second section having a second length in a direction from said first end to said second end, said third section having a third length in a direction from said first end to said second end;

a first annular flow director extending radially inwardly from the inner wall of said tubular housing at the intersection of said first section and said second section, and a second annular flow director extending radially inwardly from the inner wall at the intersection of said second section and said third section; and a plurality of filter media sections within the tubular housing and radially contained by said inner wall, each of said plurality of filter media sections having a filter media composition, wherein at least one of said plurality of filter media sections has a length in a direction from said first end to said second end that includes at least portions of at least two of said lengths of the inner wall sections such that said at least one of said plurality of media sections traverses at least one of said first and second annular flow director.

23. The filter cartridge assembly of claim 22, wherein said assembly further comprises:

a first connector that seals the first end of said tubular housing except at a centrally-located entrance port in said connector where fluid is capable of entering the assembly; and a second connector that seals the second end of said tubular body except at a centrally-located exit port where fluid is capable of exiting the cartridge.

24. The filter cartridge assembly of claim 23, wherein said assembly further contains a dialysate fluid.

25. The filter cartridge assembly of claim 22, wherein said tubular housing comprises a plastic material.

26. The filter cartridge assembly of claim 25, wherein said plastic material comprises a polypropylene material.

27. The filter cartridge assembly of claim 22, wherein the thickness of said inner wall is less than, or equal to, about 0.125 inch.

28. The filter cartridge assembly of claim 22, wherein said at least one of said plurality of filter media sections traverses said first annular flow director, wherein at least another one of said plurality of filter media sections includes a different filter media composition than said at least one of said plurality of filter media sections, said at least another one of said plurality of filter media sections has a length in a direction from said first end to said second end that includes at Least portions of said second length and said third length of said inner wall sections, and said at least another one of said plurality of filter media sections traverses said second annular flow director.

29. A system including the filter cartridge assembly of claim 23, in combination with a fluid circulating device, wherein said device has an outlet and an inlet, said entrance port is in fluid communication with said outlet, and said exit port is in fluid communication with said inlet.

30. A method of preparing the assembly of claim 23, comprising:

providing said tubular housing;

sealing one of said first and second end connectors to said tubular housing;

introducing at least one of said plurality of said filter media sections into said tubular housing;

settling said at least one of said plurality of filter media sections in said tubular housing; and sealing the other of said first and second connectors to said tubular body.

31. The assembly of claim 1, wherein said filter media composition in at least two of said filter media sections is different from each other.

32. The assembly of claim 1, wherein said plurality of filter media sections comprises an activated carbon section, an immobilized enzyme section, a powdered alumina section, a zirconium phosphate section, and a sodium zirconium carbonate or a mixture of hydrous zirconium oxide of the acetate form and sodium zirconium carbonate section, in any order.

33. The assembly of claim 1, wherein said plurality of filter media sections includes an arrangement, starting from said first end and ending with said second end, an activated carbon section, an immobilized enzyme section, a powdered alumina section, a zirconium phosphate section, and a sodium zirconium carbonate or a mixture of hydrous zirconium oxide of the acetate form and sodium zirconium carbonate section.

34. The assembly of claim 1, wherein said at least one of said plurality of filter media sections comprises a sodium zirconium carbonate.

35. The assembly of claim 1, wherein said at least one of said plurality of filter media sections comprises a zirconium phosphate.

36. The assembly of claim 22, wherein said filter media composition in at least two of said filter media sections is different from each other.

37. The assembly of claim 22, wherein said plurality of filter media sections comprises an activated carbon section, an immobilized enzyme section, a powdered alumina section, a zirconium phosphate section, and a sodium zirconium carbonate or a mixture of hydrous zirconium oxide of the acetate form and sodium zirconium carbonate section, in any order.

38. The assembly of claim 22, wherein said plurality of filter media sections includes an arrangement, starting from said first end and ending with said second end, an activated carbon section, an immobilized enzyme section, a powdered alumina section, a zirconium phosphate section, and a sodium zirconium carbonate or a mixture of hydrous zirconium oxide of the acetate form and sodium zirconium carbonate section.

39. The assembly of claim 22, wherein said at least one of said plurality of filter media sections comprises a sodium zirconium carbonate.

40. The assembly of claim 22, wherein said at least one of said plurality of filter media sections comprises a zirconium phosphate.

41. The assembly of claim 12, wherein said filter media composition in at least two of said filter media sections is different from each other.

42. The assembly of claim 12, wherein said plurality of filter media sections comprises an activated carbon section, an immobilized enzyme section, a powdered alumina section, a zirconium phosphate section, and a sodium zirconium carbonate or a mixture of hydrous zirconium oxide of the acetate form and sodium zirconium carbonate section, in any order.

43. The assembly of claim 12, wherein said plurality of filter media sections includes an arrangement, starting from said first end and ending with said second end, an activated carbon section, an immobilized enzyme section, a powdered alumina section, a zirconium phosphate section, and a sodium zirconium carbonate or a mixture of hydrous zirconium oxide of the acetate form and sodium zirconium carbonate section.

44. The assembly of claim 12, wherein said at least one of said plurality of filter media sections comprises a sodium zirconium carbonate.

45. The assembly of claim 12, wherein said at least one of said plurality of filter media sections comprises a zirconium phosphate.

* * * * *

UNITED STATES PATENT AND TRADEMARK OFFICE
CERTIFICATE OF CORRECTION

PATENT NO. : 6,878,283 B2
DATED : April 12, 2005
INVENTOR(S) : Thompson

It is certified that error appears in the above-identified patent and that said Letters Patent is hereby corrected as shown below:

Column 12,
Line 36, "tile" should read -- the --.

Column 14,
Line 49, "Least" should read -- least --.

Signed and Sealed this

Seventh Day of June, 2005

JON W. DUDAS
*Director of the United States Patent and Trademark Office*